(12) United States Patent
Cross et al.

(10) Patent No.: US 9,333,306 B2
(45) Date of Patent: May 10, 2016

(54) NEEDLE ASSEMBLY

(75) Inventors: David John Cross, Northhampton (GB); Malcolm Stanley Boyd, Wellesbourne (GB); Alasdair George Young, Chipping Norton (GB); Naceur Rekaya, Leamington Spa (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 825 days.

(21) Appl. No.: 13/581,567

(22) PCT Filed: Mar. 23, 2011

(86) PCT No.: PCT/EP2011/054419
§ 371 (c)(1),
(2), (4) Date: Oct. 31, 2012

(87) PCT Pub. No.: WO2011/117283
PCT Pub. Date: Sep. 29, 2011

(65) Prior Publication Data
US 2013/0046246 A1    Feb. 21, 2013

Related U.S. Application Data

(60) Provisional application No. 61/317,548, filed on Mar. 25, 2010.

(30) Foreign Application Priority Data

Jul. 21, 2010 (EP) ..................................... 10170281

(51) Int. Cl.
*A61M 5/32*    (2006.01)
(52) U.S. Cl.
CPC ............. *A61M 5/326* (2013.01); *A61M 5/3272* (2013.01); *A61M 2005/3247* (2013.01); *A61M 2005/3267* (2013.01); *A61M 2205/581* (2013.01); *A61M 2205/582* (2013.01); *A61M 2205/584* (2013.01)

(58) Field of Classification Search
CPC ........... A61M 5/31; A61M 5/32; A61M 5/34; A61M 5/326; A61M 5/3269; A61M 5/3271; A61M 5/3274
USPC .................................................. 604/198, 189
See application file for complete search history.

(56) References Cited

U.S. PATENT DOCUMENTS 4,702,738 A * 10/1987 Spencer ......................... 604/198
4,946,446 A *  8/1990 Vadher ........................... 604/198
(Continued)

FOREIGN PATENT DOCUMENTS

CN    1668351    9/2005
DE   20006251    8/2001
(Continued)

OTHER PUBLICATIONS

International Preliminary Report on Patentability for Int. App. No. PCT/EP2011/054419, mailed Oct. 4, 2012.
(Continued)

*Primary Examiner* — Edelmira Bosques
(74) *Attorney, Agent, or Firm* — McDonnell Boehnen Hulbert & Berghoff LLP

(57) ABSTRACT

Disclosed is a safety needle assembly has a needle guard that prevents accidental needle sticks before and after an injection. A locking collar rotates during use as an inner protrusion follows three paths of a track located on the outer surface of a body housing. When the inner facing protrusion is in the third path, it encounters a hard stop and a rotational bias that locks the guard from further retraction and, thus, covers the sharp distal end of the needle.

16 Claims, 6 Drawing Sheets

(56) References Cited

U.S. PATENT DOCUMENTS

| | | | |
|---|---|---|---|
| 5,104,386 A * | 4/1992 | Alzain | A61M 5/178 604/198 |
| 5,389,085 A * | 2/1995 | D'Alessio et al. | 604/198 |
| 5,415,645 A | 5/1995 | Friend et al. | |
| 2005/0165353 A1 | 7/2005 | Pessin | |

FOREIGN PATENT DOCUMENTS

| | | |
|---|---|---|
| JP | 2005-510308 | 4/2005 |
| WO | 01/91837 | 12/2001 |
| WO | 03/045480 | 6/2003 |
| WO | 03/097136 | 11/2003 |
| WO | 2008/127195 | 10/2008 |
| WO | 2009/144546 | 12/2009 |

OTHER PUBLICATIONS

Japanese Office Action for JP App. No. 2013-500486, mailed Jan. 6, 2015.

International Search Report and Written Opinion for Int. App. No. PCT/EP2011/054419, mailed Sep. 27, 2011.

* cited by examiner

NEEDLE ASSEMBLY

CROSS REFERENCE TO RELATED APPLICATIONS

The present application is a U.S. National Phase Application pursuant to 35 U.S.C. §371 of International Application No. PCT/EP2011/054419 filed Mar. 23, 2011, which claims priority to U.S. Provisional Patent Application No. 61/317,548 filed on Mar. 25, 2010 and European Patent Application No. 10170281.9 filed Jul. 21, 2010. The entire disclosure contents of these applications are herewith incorporated by reference into the present application.

FIELD OF THE INVENTION

Specific embodiments of this disclosure relate to an improved needle assembly, specifically a pen needle and safety shield system, but not exclusively, adapted for pen injectors. Specifically, our disclosure concerns a needle assembly that prevents accidental needle sticks before and after use. The safety shield system of this disclosure includes a retractable generally tubular guard or shield that is spring biased to normally enclose the cannula mounted in the assembly, but which locks in the extended position enclosing the cannula following injection.

BACKGROUND

Needle assemblies are commonly used to either inject substances into or extract substances out of human or animal bodies. Such needle assemblies are typically disposable and are discarded after only one use. The problem presented by the disposal of a needle assembly, and indeed, by any handling of the needle assembly, is the potential risk of being injured by the sharp end of the cannula. This is particular dangerous for health care professionals (HCPs) or similar care givers following the penetration of the skin because the needle cannula may become contaminated with body fluids and therefore capable of spreading diseases such as hepatitis and HIV. A number of safety needle assemblies have been developed where a telescopically movable shield conceals the needle cannula during the injection.

Hypodermic syringes have been used for many years to deliver selected doses of fluids including liquid medicaments, inoculations, etc. to patients. However, many applications using hypodermic needles are self-administered, including, for example, insulin, antihistamines, et cetera. The required manipulation of a standard prior art hypodermic syringe can be inconvenient, particularly where the injection is self-administered in a public environment. Medication delivery pens or pen injectors have therefore been developed to facilitate self-administration of injections. A typical pen injector includes a generally tubular body portion resembling a fountain pen that receives a vial of fluid, such as insulin, antihistamines, et cetera, having a pierceable closure, such as a rubber septum. The pen needle may include a hub generally having a double-ended cannula including a first end that extends into the body portion of the pen injector for piercing the closure of the vial and a second end used for injection of the fluid contained in the vial. The pen needle also may include a removable cup-shaped cap that encloses the second end of the needle cannula prior to use.

Various improvements in pen needles have been developed or proposed by the prior art since their introduction. Various safety shield systems have also been developed or proposed by the prior art for conventional hypodermic syringes, wherein a tubular shield is spring biased to enclose the needle cannula following injection and including safety shields which lock in the extended enclosed position following injection. Such safety shield systems for conventional hypodermic syringes are operated manually, thus requiring additional action (active systems), such as force, to activate as compared to the standard injection process. Hand manipulated safety shield systems may include spiral or complicated channel-shaped tracks on an inside surface of the shield which guide the shield during extension of the shield to enclose the needle cannula and to lock the shield in the extended position. However, such complicated systems may not always be reliable. There are also safety pen needle systems known that are automatic in nature, whereby, when the shield is retracted to its initial position, the needle is locked from further use. It would be desirable to simplify the operation of such known devices to eliminate manual manipulation or rotational movement of the shield from the retracted position to a locked extended position and to improve upon the smoothness of operation. Likewise, it would be beneficial to provide the user with audible and/or tactile feedback during use and to have a reliable locking mechanism.

The needle assembly of the present disclosure solves these problems by providing a safety shield which normally encloses the needle cannula prior to use, permits refraction of the safety shield during injection, provides audible and/or tactile feedback during the insertion stroke and provides a secure locking feature that locks the shield in the extended enclosed position following use. By incorporating the locking element as part of a rotating collar, it can additionally easily serve the purpose of indicating device status through visual indicia.

Moreover, our disclosure comprises one or more inwardly facing protrusions on a locking collar that allow the needle assembly to have the biasing member located on the outside of the main housing. This further provides the use of tracks and blocking surfaces located on the outside of the housing instead on the inner surface of the housing, thus allowing the biasing member to have a much wider inner diameter. This also has the advantage of providing additional space in the center of the needle shield, e.g. a cavity, that can be used for several features, preferably for introducing a drug container. Since there is no limiting factor for the biasing member diameter, this provides more design variation in setting up the retraction force of the needle guard to aid in the user's convenience.

These and other advantages and features will become evident from the following more detailed description of the invention.

One problem to be solved by the present invention is to provide a needle assembly and a drug delivery device where the safety and comfort of the user is increased.

SUMMARY

The disclosed needle assembly may contain a needle guard that can reduce the risk of accidental needle sticks before and after use as well as reduce the anxiety of users suffering from needle phobia. The guard is preferably configured with a solid planar surface at its distal end that provides a large surface area that may reduce the pressure exerted on the patient's skin, which allows the user to experience an apparent reduction in the force exerted against the skin. Preferably, the planar surface covers the entire distal end of the guard with the exception of a small needle pass through hole aligned axially with the needle. This pass through hole is preferably no more than 10 times greater in diameter than the outer diameter of the needle cannula. For example, with a needle outside diameter of 0.34 mm, the pass through hole diameter D can be 3.4 mm. Preferably, the pass through hole size should be large enough for the user to see that the device is primed, e.g. the user may be able to see a drop or more of medicament. This difference between the hole size and cannula diameter is to allow for tolerances and also to allow users to see the drop of liquid on the end of the cannula after priming. Further, the movable guard or shield is configured to move axially in both the distal and proximal directions when pressed against an injection site. When the needle assembly is removed or withdrawn from the patient, the guard may be returned to its original starting location and may be securely locked with respect to the housing. This may be achieved by a rotating locking collar, that may securely lock into the housing through one or more inwardly projecting protrusions or pips such that the guard will be locked from further substantial axial, in particular proximal, movement. By "substantial" movement we do not mean the typically amount of "play" in system, but instead we mean that the guard does not move axially a distance that exposes the distal end of the cannula.

According to one aspect, a needle assembly is provided. The needle assembly may be, preferably releasably, attachable to a drug delivery device. The needle assembly may comprise a housing. The housing may have an outer surface. The housing may have a proximal end and a distal end. At least one track, preferably two or more tracks, may be provided on the housing. The at least one track may be provided on the outer surface of the housing. The housing, preferably the proximal end of the housing, may have a connector. The connector may be configured for, preferably releasable attachment to the drug delivery device. The needle assembly may comprise at least one needle cannula. The needle assembly may comprise a locking collar. The locking collar may have a bearing surface. The locking collar may have an inner surface. The locking collar, in particular the inner surface of the locking collar, may comprise at least one, preferably inwardly facing, protrusion. In particular, the number of protrusions may correspond to the number of tracks provided on the housing. The at least one protrusion may be configured to mechanically cooperate with the at least one track. In particular, each protrusion may be configured to mechanically cooperate with one respective track. The needle assembly may comprise a needle guard. The needle guard may be adapted and arranged to provide protection of the at least one needle cannula. The needle guard may be configured to mechanically cooperate with, in particular to engage, the locking collar through the bearing surface.

According to one embodiment, the needle cannula comprises a measurable diameter. The needle cannula may be configured to be mounted in the housing. The needle guard may comprise a hole where a needle can pass through. The needle pass through hole may have a diameter D that is no more than ten times greater than the diameter of the needle cannula.

The needle assembly may be attachable to the drug delivery device, preferably a pen shaped injection device, comprising, the housing having the outer surface, the proximal end, and the distal end. The proximal end of the housing may have the connector configured for, preferably releasable, attachment of the needle assembly to the drug delivery device. This connector can be any connector design, such as threads, snap fits, bayonet, lure lock, or combination of these designs. The needle cannula, preferably a doubled ended needle for use with a pen type injector, is mounted in the housing having a measurable diameter. The needle cannula may be mounted inside the housing using any technique known to those skilled in the art, such as welding, gluing, friction fit, and the like.

According to one embodiment, the needle assembly comprises a biasing member. The biasing member may be adapted and arranged to exert a, preferably axial, biasing force onto the needle guard and the locking collar. The, preferably permanent, axial biasing force may be directed in the distal direction with respect to the housing. The biasing member may be configured to be engaged with the housing. One end of the biasing member may be engaged with a lip on the inner surface of the locking collar.

The assembly contains the biasing member engaged with the housing, preferably a lip or ridge located on the outer surface. A preferred biasing member is a spring, however, any type of member that produces a biasing force on the needle guard will work.

The assembly comprises one or more tracks. The at least one track may comprise a first path. The at least one track may also comprise a second path. Furthermore, the at least one track may comprise a third path. The assembly comprises one or more protruding features, e.g. protrusions, pips or the like. The number of protruding features may correspond to the number of tracks. Each protruding feature may be configured and arranged to mechanically cooperate with one respective track. In particular, one respective protruding feature may be configured and arranged to be guided by one respective track.

According to one embodiment, the needle assembly comprises one track, and one protrusion. The track may comprise a first path. The track may also comprise a second path. Furthermore, the track may comprise a third path. The first, second and third path may be connected with one another, e.g. in a way as to result in one continuous track with different sections formed by the individual paths.

According to one embodiment, the needle guard is axially moveable with respect to the housing between an extended, e.g. a distal, and a retracted, e.g. a proximal position. The protrusion may be configured to mechanically cooperate with the first and second path during retraction and partial extension of the needle guard. The protrusion may be configured to mechanically cooperate with the third path during final extension, e.g. extension after the injection, of the needle guard into a locking position. In the locking position, the needle guard may be configured to be prevented from further axial, in particular proximal, movement with respect to the housing.

According to an embodiment, the needle assembly comprises an outer sleeve. The outer sleeve may be configured to be, permanently or releasably, fixed to the housing. The outer sleeve may be configured to surround the collar and the biasing member. The outer sleeve may have at least one opening or window. The outer sleeve may comprise two, three or more openings or windows. Preferably, the outer sleeve comprises three openings or windows such that the user may be able to view the opening or window irrespective of the position of the device and, hence, the needle assembly, with respect to the user. The opening or window may be adapted and arranged for viewing indicia, e.g. symbols or numbers, provided on an outer surface of the locking collar. The indicia may be configured to indicate a pre-use ready position of the needle guard before an injection is performed. The indicia may be configured to indicate a locked position of the needle guard.

The assembly has the outer sleeve that may be axially and rotationally fixed to the housing and that may surround the locking collar and biasing member. The outer sleeve may have the opening or window that allows the user to view markings, color or other indicia on the outer surface of the locking collar before and/or after use. Preferably, user noticeable indicia indicate both the pre-use position (i.e. ready to use or unused) and the post-use locked position (i.e. used) of the guard after the assembly has been used to perform an injection.

According to an embodiment, the bearing surface comprises a crown. The crown may be arranged on the inner surface of the locking collar. The crown may be configured to mechanically cooperate, in particular to engage, with a plurality of angled surfaces. The angled surfaces may be arranged on the proximal end of the needle guard. The crown may be configured to mechanically cooperate with the plurality of angled surfaces to rotationally bias the collar.

According to an embodiment, the locking collar is configured to rotate when the protrusion moves from the first path to the second path. Additionally or alternatively, the locking collar may be configured to rotate under a biasing torque created by mechanical interaction between the needle guard and the locking collar due to the, preferably permanent, axial biasing force exerted on the locking collar and the needle guard by the biasing member. Additionally or alternatively, the locking collar may be configured to rotate under a biasing torque created by the biasing member or an additional biasing member.

To prevent reuse of the needle assembly, the disclosure includes the previously mentioned locking collar. The locking collar may have the inner surface that surrounds a portion of the housing and is free to rotate within the defined track area on the outside surface of the housing. The inner surface of the collar can have the bearing surface, such as the crown. Furthermore, the inner surface of the collar can have the inner facing protrusion or pip that is slidably engaged with the track on the outer surface of the housing. Preferably, the crown comprises a number of distal facing angled surfaces (so-called "dog teeth") that act as bearing surfaces. These teeth interact with the similarly angled faces on the needle guard and cause the collar to experience a torque that is initially resisted by the interaction of the protrusion within the track when the needle assembly is used. The needle guard has a distal end and a proximal end, where the proximal end comprises the plurality of angled surfaces (i.e. another corresponding set of dog teeth) that are suitable to engage and bias the crown on the locking collar both rotationally and axially. One end of the biasing member is engaged with the lip on the inside surface of the locking collar and the other end is engaged with the housing near the proximal end.

According to one embodiment, the needle guard is always rotationally constrained by the outer sleeve. The locking collar may be rotationally constrained when the protrusion mechanically cooperates with the first path of the track. The assembly may provide an audible and/or tactile indication to a user when the locking collar rotates as the protrusion moves from the first path to the second path.

Preferably, the one or more tracks located on the outside surface of the housing has one or more sets of first, second and third paths. The one or more protrusions on the inner surface of the locking collar may travel in the first and second paths during retraction and partial extension of the guard. The protrusion may move to the third path and into a locking position, e.g. an axial position where it is prevented from further axial and rotational movement, when the guard is fully extended. The guard may be, preferably permanently, rotationally constrained by the outer sleeve, preferably by the use of one or more spline features in the outer surface of the guard in cooperation with one or more followers or pips located at the distal end of the outer sleeve. The locking collar may be rotationally constrained when the protrusion is in the first path of the track. As the protrusion is moved axially in the proximal direction when the guard pushes the locking collar during retraction, the protrusion moves from the first track to the second track causing the assembly to emit an audile sound and/or tactile feedback. This tells the user that the device may now have been activated to lock upon extension of the guard in the distal direction.

According to one embodiment, when the protrusion mechanically cooperates with the third path, the crown and the angled surfaces on the needle guard are configured to mechanically cooperate with each other. The collar and the needle guard may be in preferably permanent, biasing relationship provided by the biasing member such that the needle guard is prevented from further axial, in particular proximal, movement, the needle assembly thus being in a post-use lock out state.

According to one embodiment, the housing comprises an upper body. The housing may comprise a lower body. The lower body may be, releasably or permanently, connected to the upper body.

According to one embodiment, the biasing member is adapted and arranged to be, permanently or releasably, engaged with the lower body. Additionally or alternatively, the biasing member may be adapted and arranged to be, permanently or releasably, engaged with the upper body. The outer sleeve may be configured to be, permanently or releasably, fixed to the lower body.

According to one embodiment, the at least one track or at least a portion of the at least one track may be provided by the upper body, in particular an outer surface of the upper body. Additionally or alternatively, the at least one track or at least a portion of the at least one track may be provided by the lower body, in particular an outer surface of the lower body The arrangement of the upper body and the lower body may provide on its outer surface at least one, preferably two or more tracks.

The bearing surface on the locking collar may engage the proximal end of the guard. The inner surface of the locking collar may comprise the lip to engage the biasing member. The inner surface may have the inner facing protrusion that is slidably engaged with the track that is on the outer surfaces of the lower and upper bodies.

According to one embodiment, the assembly comprises an inner cavity. The inner cavity may be provided by the upper body and/or the lower body.

In yet another embodiment, there is provided a needle assembly attachable to a drug delivery device, comprising an upper body having an outer surface, a proximal end, and a distal end, where the proximal end may have a connector configured for attachment to the drug delivery device. A lower body having an outer surface is connected to the upper body such that it is in the same plane as a portion of the upper body outer surface. The outer surfaces of both the upper body and the lower body together may form the track The proximal end of the lower body may have the connector for attachment to the drug delivery device or, alternatively, both the upper and lower bodies could share the connector. A needle cannula is mounted on the inside of the upper body. A spring or other biasing member is engaged with a portion of the outer surface of the lower body. The biasing member is also engaged with a locking collar, preferably through a lip located on the inner surface, where the inner surface also has a protrusion that is slidably engaged with a track that is formed on the outer surfaces of both the lower and upper bodies.

A needle guard or shield may be also part of this alternative embodiment, which has a distal end and a proximal end, where the proximal end engages a bearing surface on the distal end of the locking collar. An outer sleeve may be rotationally and axially fixed to the lower body and may be configured to surround the locking collar and biasing member, and to retain the guard in the assembly against the biasing force.

According to a preferred embodiment, a needle assembly is provided which is attachable to a drug delivery device. The needle assembly comprises a housing having an outer surface, a proximal end, and a distal end. At least one track is provided on the outer surface of the housing. The needle assembly comprises at least one needle cannula. The needle assembly comprises a locking collar having a bearing surface and an inner surface, where the inner surface comprises at least one protrusion. Each protrusion is configured to mechanically cooperate with one respective track. The needle assembly comprises a needle guard adapted and arranged to provide protection of the at least one needle cannula, the needle guard being configured to engage the locking collar through the bearing surface.

According to another embodiment, a needle assembly is provided which is attachable to a drug delivery device. The needle assembly comprises a housing having an outer surface, a proximal end, and a distal end. The needle assembly comprises a needle cannula having a measurable diameter mounted in the housing. The needle assembly comprises a biasing member engaged with the housing. The needle assembly comprises a locking collar having a bearing surface and an inner surface, where the inner surface has an inwardly facing protrusion that is slidably engaged with a track on the outer surface of the housing. The needle assembly comprises a guard having a distal end and a proximal end, where the proximal end engages the locking collar through the bearing surface. The needle assembly comprises an outer sleeve fixed to the housing that surrounds the locking collar and biasing member.

These as well as other embodiments of various aspects of the present invention will become apparent to those of ordinary skill in the art by reading the following detailed description, with appropriate reference to the accompanying figures.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE FIGURES

Exemplary embodiments are described herein with reference to the figures, in which.

DETAILED DESCRIPTION

Figure 1:
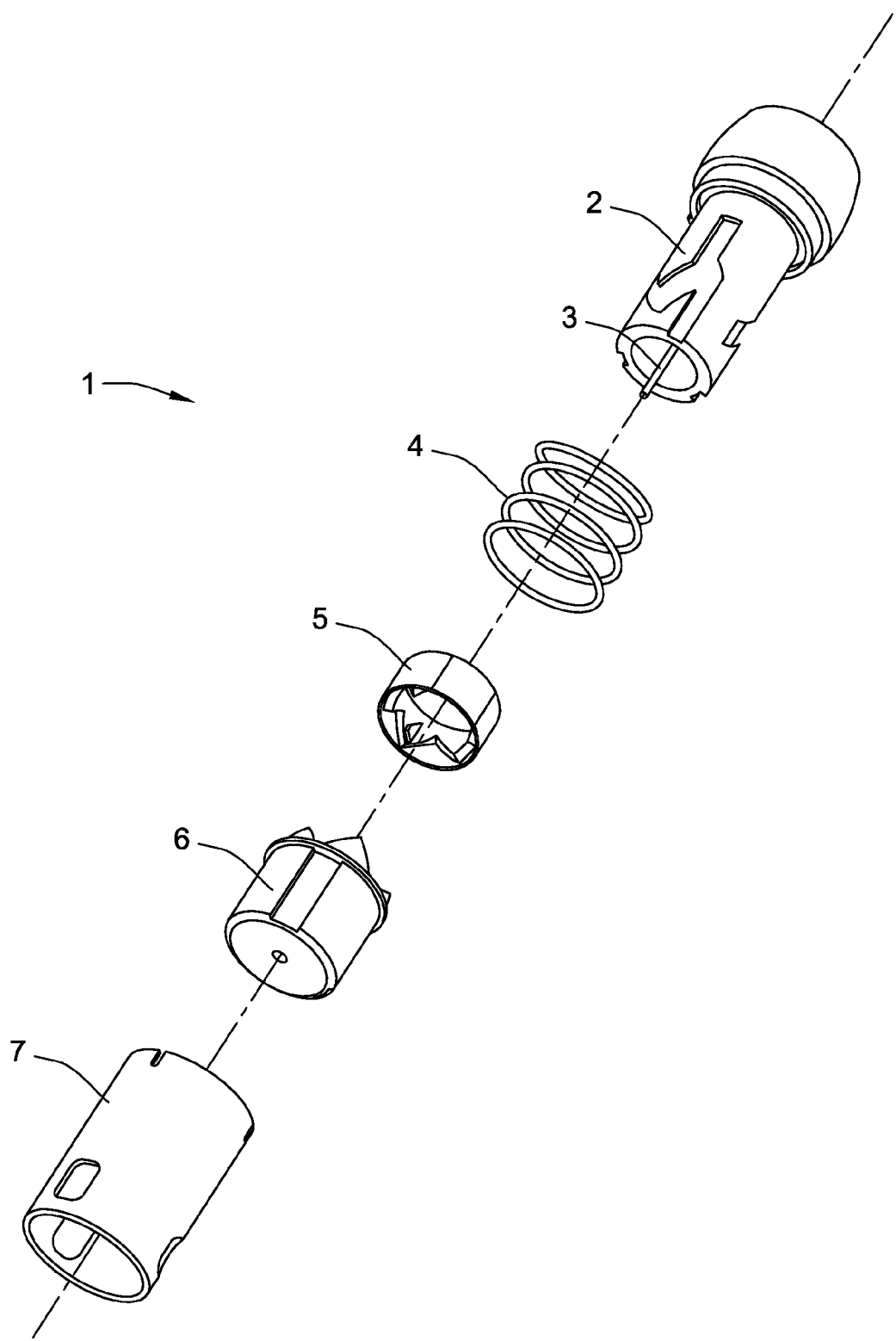
FIG. 1 illustrates an exploded perspective view of one possible needle assembly.
Figure 2:
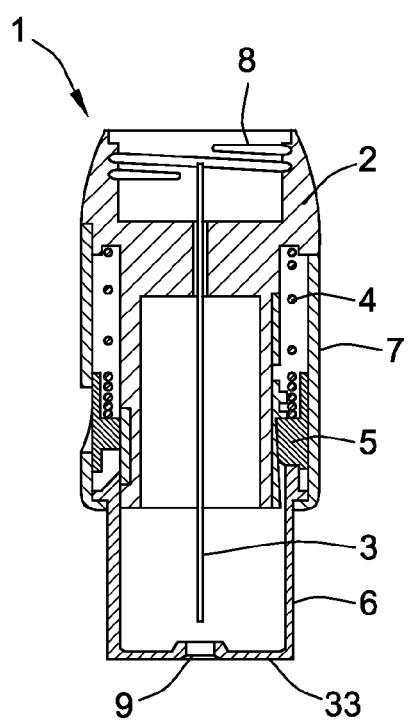
FIG. 2 illustrates a cross-sectional view of the embodiment of FIG. 1.

FIG. 1 shows an exploded view of one possible embodiment of the needle assembly 1 comprising six parts: a housing 2, a needle cannula 3 mounted inside the housing 2, a biasing member 4, shown as a compression spring, a rotatable locking collar 5, a needle guard 6, and an outer sleeve 7. FIG. 2 shows these parts assembled in a cross-sectional view, where the outer sleeve 7 is rotationally and axially fixed to the housing 2 and acts to hold the parts of the assembly together. A connector 8, shown as threads, is located at the proximal end of housing 2. The connector 8 is configured for attachment to a drug delivery device. The compression spring 4 and locking collar 5 are assembled onto the housing 2 prior to connecting the outer sleeve 7 forming one sub-assembly. The needle guard 6 is slidably assembled to the inside of the outer sleeve 7 to form a second sub-assembly. Once assembled, the housing 2 and outer sleeve 7 are securely fixed such that they form a single unit. The two sub-assemblies can be connected together in any manner known to the art, preferably using a snap fit, however these sub-assemblies can be welded, glued, friction pressed, or pinned together. Regardless of the manner of attachment, the compression spring 4, locking collar 5, and needle guard 6 may all be able to move within these body components.

The compression spring 4 acts between the housing 2 and the locking collar 5 to axially bias the needle guard 6 into an extended (guarded) position as illustrated in FIG. 2. The distal end of the spring 4 engages an inner lip 30 arranged on the inner surface 13 of collar 5. The proximal end of the spring 4 engages a groove 27 of the housing 2.

Figure 3:
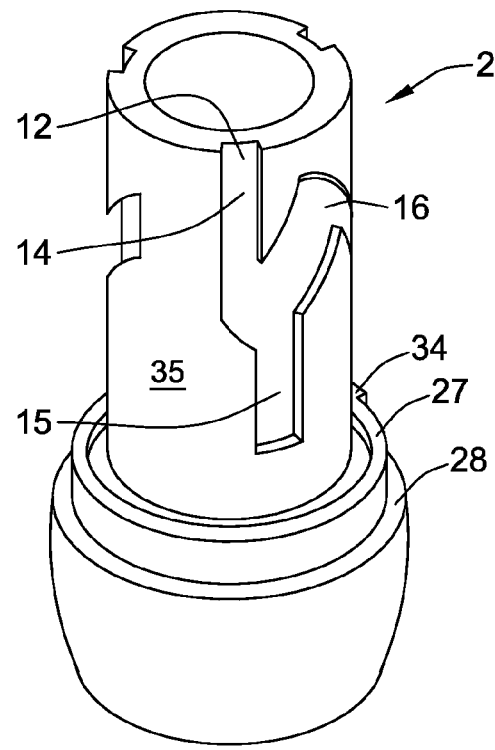
FIG. 3 illustrates the housing of the embodiment of FIG. 1.

The locking collar 5 has a crown 10 that comprises one or more inwardly protruding features, protrusions, pips, or like structures 11. Said protruding features 11 run in one or more tracks 12 or guide ways formed in the outer surface 35 of the housing 2. As shown in FIG. 3, track 12 has three paths, 14, 15, and 16, that have a specific geometry such that after a single use of the needle assembly 1, the inwardly protruding feature 11 is blocked from further axial movement and the guard 6 (and, thus, the device) is "locked" in a guarded, e.g. distal, position, where the distal end of the needle 3 is completely and safely covered by the guard 6. The crown 10 comprises one or more angled distal facing bearing surfaces to engage like surfaces facing proximally on guard 6.

Figure 5:
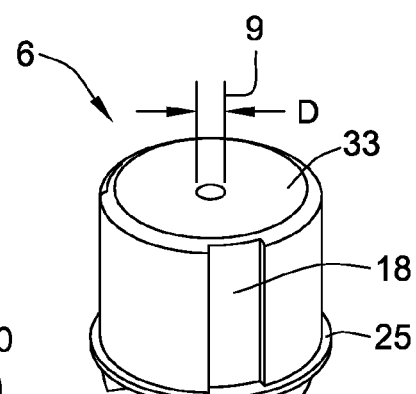
FIG. 5 illustrates a perspective view of the guard of the embodiment of FIG. 1.
Figure 6:
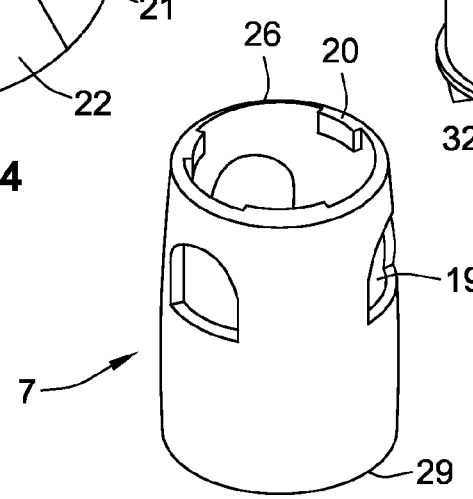
FIG. 6 illustrates a perspective view of the outer sleeve of the embodiment of FIG. 1.

The needle guard 6 is, preferably permanently, rotationally constrained by the outer sleeve 7 through a splined engagement of one or more protrusions 20 of the outer sleeve 7 in one or more slots 18 of the guard 6 (see FIGS. 5 & 6). Although spring 4, preferably permanently, biases guard 6 in the distal direction, the guard 6 is retained in the outer sleeve 7 by interaction between retention ridge 26 on the distal end of outer sleeve 7 and proximal lip 25 of the guard 6. A crown 17 at the proximal end of the needle guard 6 interacts through proximally facing bearing surfaces 32 or "dog teeth" with the similarly shaped crown 10 formed on the inside of the locking collar 5.

Figure 7:
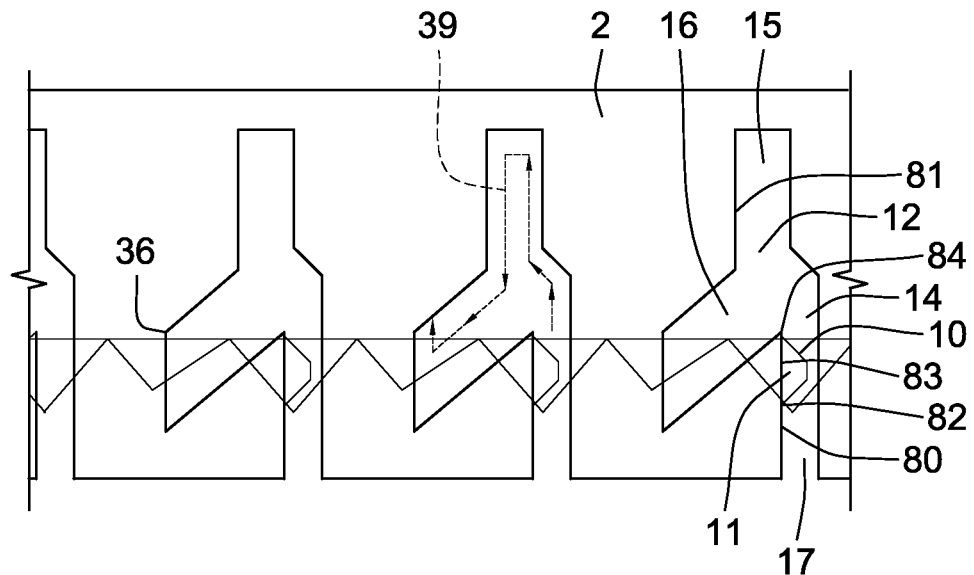
FIG. 7 illustrates the paths of the tracks and the starting position of the protrusions of the embodiment of FIG. 1.

One unique feature of the needle assembly 1 is the user feedback that is given when the assembly 1 is used. In particular, the assembly 1 emits an audible and/or tactile "click" to indicate to the user that the needle guard 6 will lock safely out upon completion of the injection. This audible and/or tactile feature works as follows. As mentioned, the needle guard 6 is, preferably permanently, rotationally constrained by the outer sleeve 7. The set of dog teeth 32 on the crown 17 at the proximal end of the needle guard 6 interacts with a similar set of dog teeth 31 formed on the inside of the locking collar 5. In the initial position, the two sets of teeth 31, 32 are unable to completely mesh, i.e. they are in an axially biased engagement. In particular, the dog teeth 31, 32 are kept in distance and pushed or pressed together due to the biasing force exerted by the spring 4, as best shown by FIG. 7. Likewise, guard 6 is rotationally constrained by outer sleeve 7 and the collar 5 is rotationally constrained by its inwardly facing protrusion 11 interacting with path 14 of track 12. In particular, the spring 4 applies force in the distal direction on the proximal end of locking collar 5 such that the collar 5 is urged to move axially and is rotationally biased along the angled bearing surfaces 31 and 32. Due to the angled surfaces of dog teeth 31, 31, the axially directed force may tend to induce a rotation of the locking collar 5. However, this rotation may be prevented due to mechanical cooperation of the protrusion 11 and path 14 of track 12. In particular, the dog teeth 31 and 32 are prevented from meshing because face 83 of protrusion 11 is biased against wall 80. As the guard 6 pushes the locking collar 5 in the proximal direction, protrusion 11 will move proximal along path 14 until the lower most edge 82 moves past point 84 on path 14. Once edge 82 clears point 84 following along track 12 as indicated by arrow 39, the locking collar 5, along with protrusion 11, is free to rotate as the dog teeth 31, 32 try to mesh. This causes face 83 of protrusion 11 to collide with wall 81 of path 15, which provides an audible sound, as well as a tactile feel, to the user indicating that the device is now ready for injection. The rotational torque generated by the interaction of the dog teeth 31 and 32, in particular the angled surfaces of the dog teeth 32, 32, converts axial movement of the needle guard 6 into rotation of the locking collar 5 such that protrusion 11 is brought into mechanical cooperation with path 15. Accordingly, no rotational bias of the locking collar 5 is required, e.g. by means of spring 4. Alternatively, the rotational torque needed to cause the rotation of the locking collar 5 may be provided by spring 4 providing the previously mentioned axial bias and, additionally, a rotational bias. Alternatively, the rotational torque needed to cause the rotation of the locking collar 5 may be provided by an additional spring (not explicitly shown) or clamping arms (not explicitly shown).

When the needle assembly 1 is used, the needle guard 6 is pushed in the proximal direction as the planar surface 33 comes into contact with an injection site or other stationary surface. This proximal movement of the guard 6 pushes the collar 5 also in the proximal direction as described above. After a predetermined distance, which is set by the intersection of paths 14 and 15, the locking collar 5 is forced to rotate under the rotational torque generated by the interaction of the dog teeth 31 and 32 due to the axially directed biasing force exerted on the collar 5 by the spring 4. As described above, the collar 5 "snaps" around (i.e. slightly rotates) as the two sets of dog teeth 31, 32 seek to become meshed. This sudden rotational movement of the collar 5 and the abrupt collision of face 83 of the inwardly facing protrusion 11 with the side wall 81 of the path 15 provides the user with the audible and/or tactile "click". Said "click" may indicate that the point of no return has been reached, i.e. when the spring 4 returns the needle guard 6 to an extended position, the, the needle guard 6 will be locked irrespective of whether an injection has been performed after the "click" or not.

As mentioned, the distal end of the guard 6 has the planar surface 33 that provides an added measure of safety and reduces the pressure exerted by the guard 6 on the injection site during an injection with the needle assembly 1. Because the planar surface 33 substantially covers access to the needle 3, a user is prevented from gaining access to the distal tip of the needle 3 after the assembly 1 is in the locked position. Preferably, the diameter D of needle pass through hole 9 in the planar surface 33 is no more than 10 times that of the outer diameter of needle cannula 3.

Figure 4:
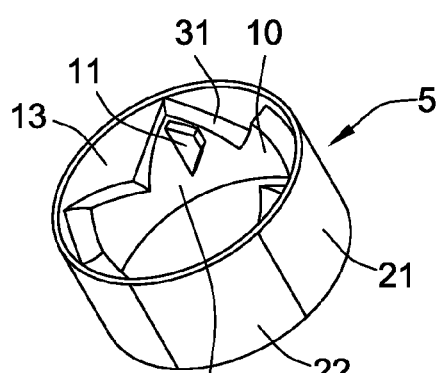
FIG. 4 illustrates a perspective view of the locking collar of the embodiment of FIG. 1.

The housing 2 also has alignment feature 34 that interacts or engages with a corresponding alignment feature (not shown) on the outer sleeve 7. Such an alignment feature 34 ensures correct positioning of the one or more windows 19 relative to locking collar 5. The collar 5 preferably has at least one indicia shown as a colored area 21 in FIG. 4. The at least one indicia is visible through the at least one opening in the outer sleeve 19. The indicia provide the user with a visual notice that the guard 6 is in a locked position. For example, a green color on the locking collar 5 in position 22 could indicate the needle assembly 1 is ready for use and a band of red color in position 21 could be used to indicate that the assembly 1 has been used and is locked. Alternatively, graphics, symbols or text could be used in place of color to provide this visual information/feedback.

Figure 8:
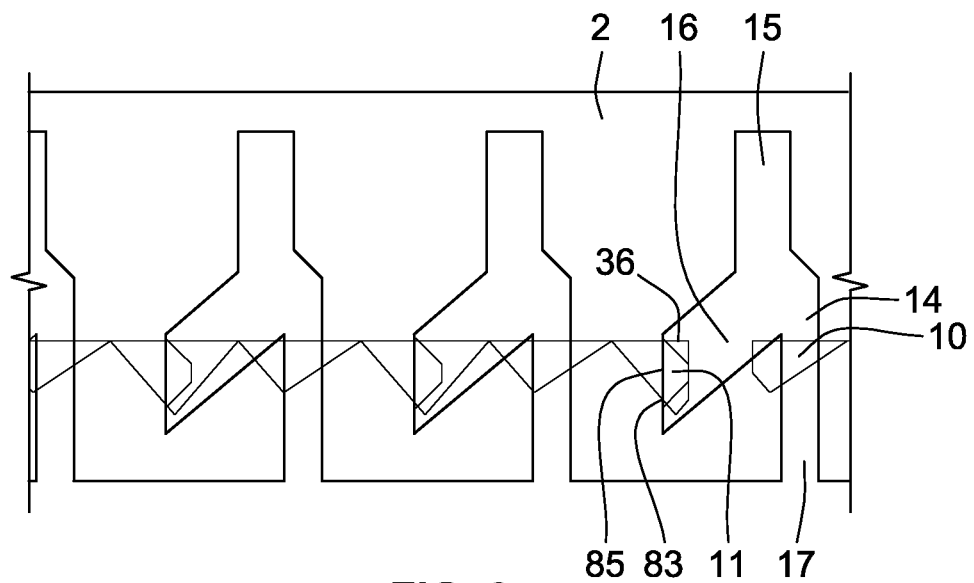
FIG. 8 illustrates the paths of the tracks and the ending position of the protrusions of the embodiment of FIG. 1.

FIGS. 7 and 8 illustrate two-dimensionally the movement (see directional arrow 39) of the inwardly facing protrusion 11 from the initial position (FIG. 7) to the final locked position (FIG. 8) as the protrusions 11 on the locking collar 5 follow the paths 14, 15, and 16 in track 12 on the outer surface 35 of the housing 2. It is within the scope of our invention that a number of tooth arrangements and/or profiles could be used to fulfill the required function such as providing the torque and/or the "click" described above, e.g., simple equal tooth profiles or more complex multi-angled profiles. The particular profile being dependent upon the required point of commit and rotation of the locking collar 5. FIGS. 7 & 8 illustrate a hard stop feature 36 in path 16 that may prevent protrusion 11 from moving proximally after an injection. This hard stopping of the locking collar 5 likewise prevents guard 6 from substantial movement proximally, as defined earlier, from its initial start position and, thus, positions the guard 6 in a "locked out" safe position completely covering the distal end of needle 3. Additionally, face 83 of protrusion 11 is biased against wall 85 of path 16, which may further prevent retraction of the guard 6 because the collar 5 is prohibited from rotating.

Figure 9:
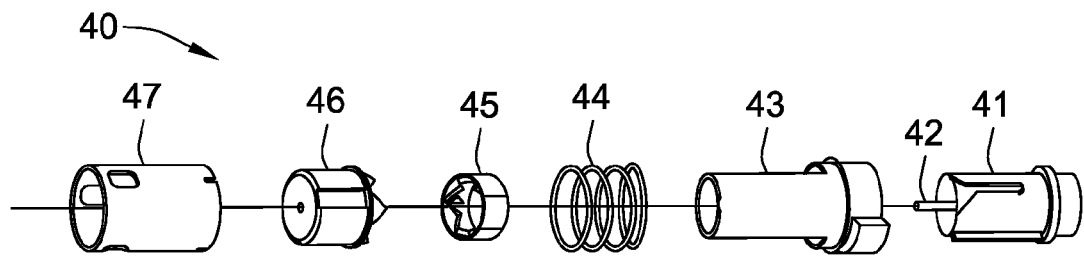
FIG. 9 illustrates an exploded perspective view of another possible needle assembly.
Figure 10:
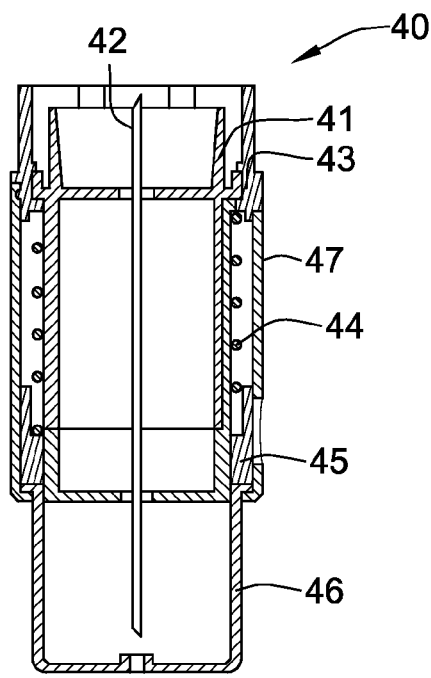
FIG. 10 illustrates a cross-sectional view of the embodiment of FIG. 9.
Figure 11:
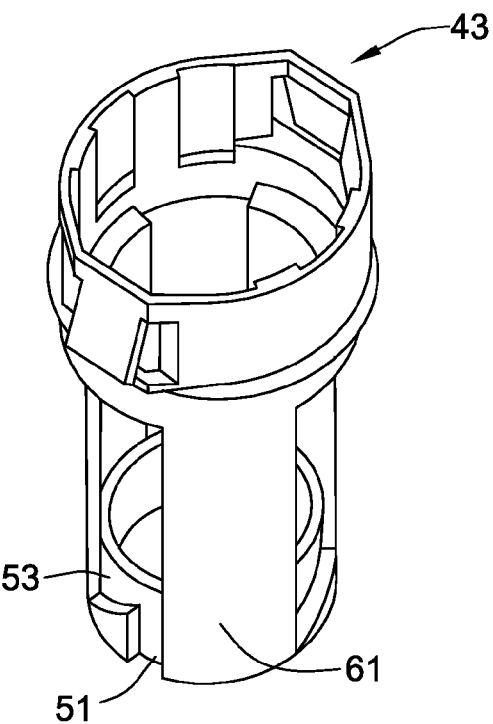
FIG. 11 illustrates the lower body of the embodiment of FIG. 9.
Figure 12:
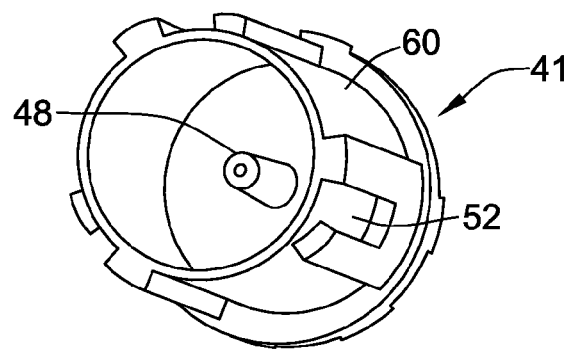
FIG. 12 illustrates the upper body of the embodiment of FIG. 9.

A second possible embodiment 40 of the needle assembly is shown in FIGS. 9-17. An exploded view of the components is shown in FIG. 9 and a cross-sectional view of the fully assembled needle assembly 40 is illustrated in FIG. 10. There is an upper body 41, a lower body 43, a needle 42, a biasing member (spring 44), a locking collar 45, with indicia 56 and 57 (see FIG. 14), a needle guard 46, and an outer sleeve 47 with one or more openings 63 (see FIG. 16) through which the indicia are visible. As with the first embodiment described above, there are, preferably, three indicator windows used to provide the user a clear indication of the status of the needle assembly 40 when viewed from any angle. For example, when the device has been used, a red color on the locking collar 45 is visible because it has moved via rotation during use and is now visible through the opening 63 in the outer sleeve 47.

Figure 15:
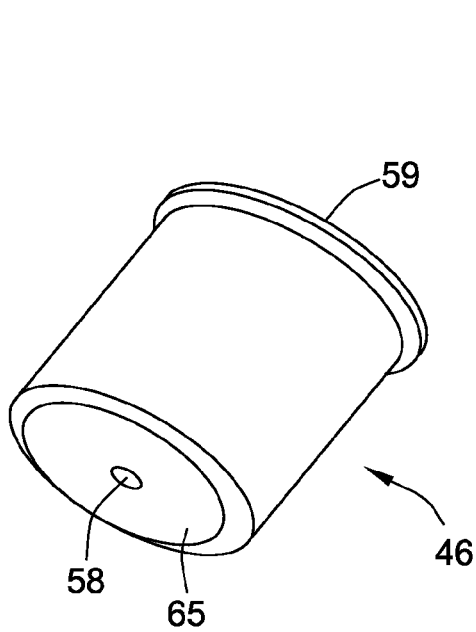
FIG. 15 illustrates a perspective view of the guard of the embodiment of FIG. 9.
Figure 16:
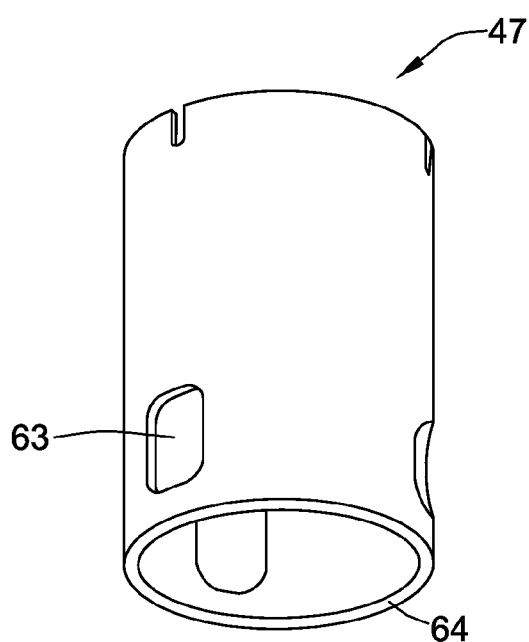
FIG. 16 illustrates a perspective view of the outer sleeve of the embodiment of FIG. 9.

Guard 46 has a lip 59 (see FIG. 15) that engages retention feature 64 on outer sleeve 47 (see FIG. 16), which keeps guard 46 of the assembly 40 biased distally by spring 44 through collar 45. Guard 46 also has a planar surface 65 with a needle access hole 58 (FIG. 15).

Needle 42 is mounted to hub 48 (see FIG. 12) on the inside of upper body 41. As illustrated, the guard 46 is not rotationally constrained, but could be if necessary. As with the first embodiment, materials of construction of the various components of our needle assemblies 1 and 40 are selected with the aim to achieve a low co-efficient of friction between the components, especially between the locking collar 45 and the needle guard 46, in order to minimize the risk that the guard 46 could be used to backwind and unlock the system after use. For example, the various components could be manufactured from polybutylene terephtalate (PBT), Polyoxymethylene (POM, acetal homopolymer, polyacetal), Polycarbonate (PC), and or combinations of these materials.

Figure 13:
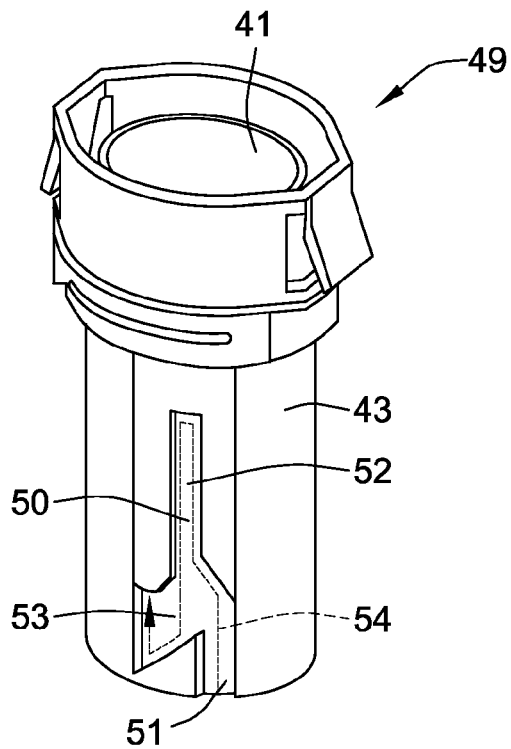
FIG. 13 illustrates the lower and upper bodies as assembled for the embodiment of FIG. 9.
Figure 14:
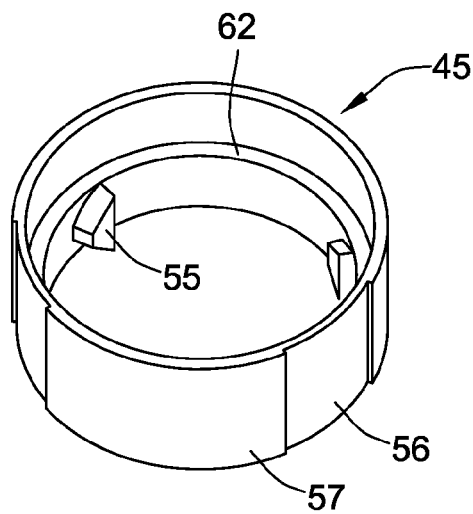
FIG. 14 illustrates a perspective view of the locking collar of the embodiment of FIG. 9.

Generally, the operation of this embodiment is very similar to that of the first embodiment described above, with the exception that the locking collar 45 and the guard 46 do not have a crown of dog teeth. Additionally, in this embodiment, as illustrated in FIG. 13, upper body 41 and lower body 43 are configured and arranged so that they nest together with the lower body 43 surrounding the upper body 41 while allowing a portion of the upper body's outer surface 60 to be in alignment or flush with the outer surface 61 of the lower body 43. Upper and lower bodies 41, 43 can be connected in any manner known to the art such as snap fit, glued, welded, or the like. Upper and lower body 41, 43 may be fixed to each other such that a cavity may be formed inside the body 41, 43. The cavity may be used to house a medicament container, e.g. a hermetically sealed capsule. The two bodies 41, 43 may be arranged such that each outer surface provides a portion of track 50 so that there will be three paths, 51, 52, and 53. The inner surface of the locking collar 45 has an inner facing protrusion 55 (see FIG. 14) that travels in track 50 following the directional arrow 54 shown in FIG. 13 during use of the needle assembly 40. This travel direction is virtually the same as described for the first embodiment. Alternatively, the collar 56 provides two or more protrusions 55 and the bodies 41, 43 provide two or more tracks 50.

Figure 17:
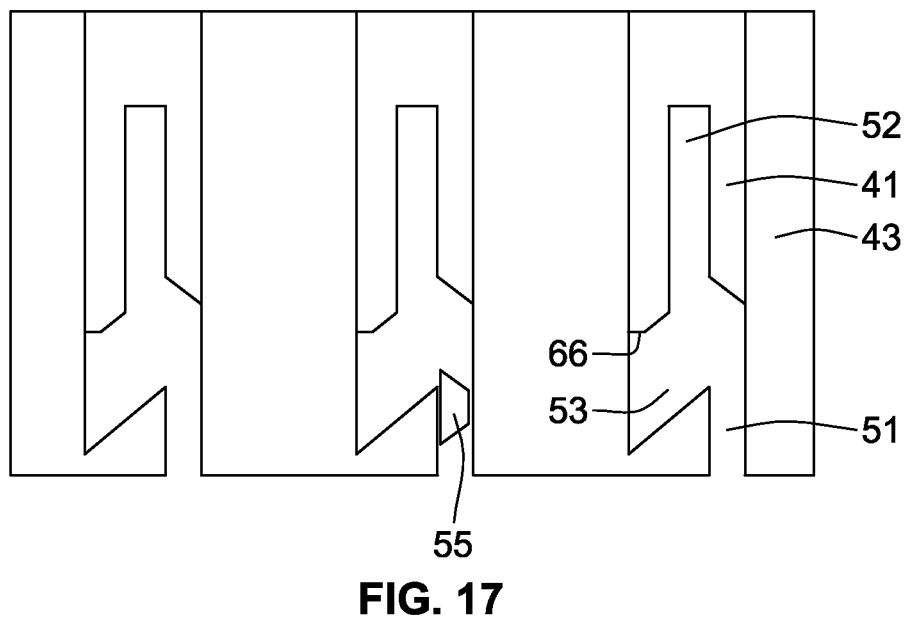
FIG. 17 illustrates the paths of the tracks and the starting position of the protrusions of the embodiment of FIG. 9.
Figure 18:
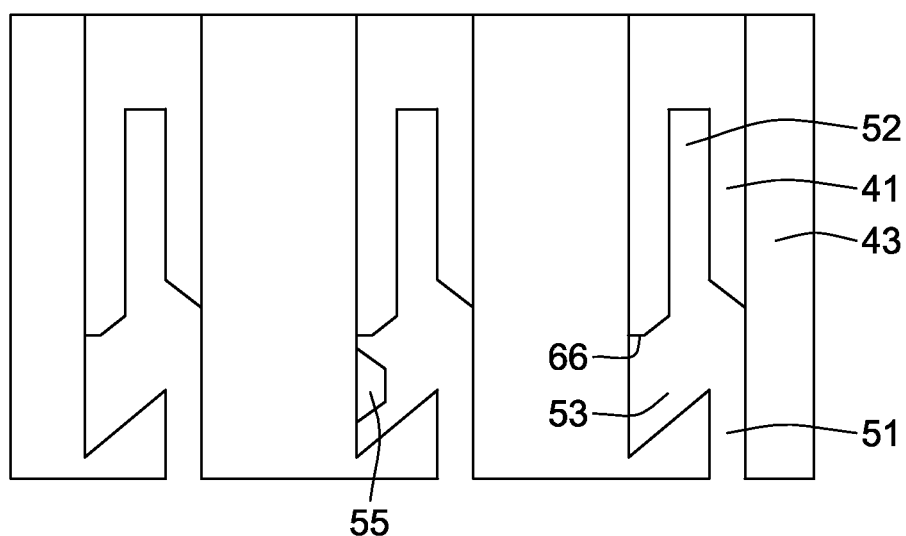
FIG. 18 illustrates the paths of the tracks and the ending position of the protrusions of the embodiment of FIG. 9.

FIGS. 17 and 18 illustrate two-dimensionally the inner facing protrusion 55 of the locking collar 45 (only one of the protrusions is shown in the figures for clarity) with track 50, which comprises portions of the outer surfaces of the upper and lower bodies 41, 43, during use of the needle assembly 40. The figures illustrate the movement of the inwardly facing protrusion 55 from the initial position (FIG. 17) to the final locked position (FIG. 18) as the protrusions 55 on the locking collar 45 follow paths 51, 52, and 53 of track 50. In this embodiment, the collar 45 is passively rotated by the track 50 guiding the protrusion 55. FIG. 18 illustrates the hard stop feature 66 in path 53 that prevents protrusion 55 from moving proximally once the guard 46 has extended to its initial position after use. This hard stopping of the locking collar 45 may likewise prevent guard 46 from moving proximally from its initial start position and, thus, positions the guard in a "locked out" safe position completely covering the distal end of needle 42.

Exemplary embodiments of the present invention have been described. Those skilled in the art will understand, however, that changes and modifications may be made to these embodiments without departing from the true scope and spirit of the present invention, which is defined by the claims.

We claim:

1. A needle assembly attachable to a drug delivery device, comprising:
 a housing having an outer surface, a proximal end, and a distal end, at least one track being provided on the outer surface of the housing;
 at least one needle cannula;
 a locking collar having an inner surface and a bearing surface arranged on the inner surface, wherein the inner surface comprises at least one protrusion which is configured to mechanically cooperate with the at least one track; and
 a needle guard adapted and arranged to provide protection of the at least one needle cannula, the needle guard comprising at least one surface arranged on a proximal end of the needle guard and configured to engage the bearing surface of the locking,
 wherein the bearing surface comprises a crown arranged on the inner surface of the locking collar, and wherein the at least one surface of the needle guard comprises a plurality of angled surfaces, the crown being configured to mechanically cooperate with the plurality of angled surfaces to rotationally bias the locking collar.

2. The needle assembly of claim 1, wherein each of the at least one protrusions is configured to mechanically cooperate with one respective track of the at least one track.

3. The needle assembly of claim 1, wherein the needle cannula comprises a measurable diameter and the needle cannula is configured to be mounted in the housing, and wherein the needle guard comprises a needle pass through hole having a diameter that is no more than ten times greater than the diameter of the needle cannula.

4. The needle assembly according claim 1, comprising a biasing member which is adapted and arranged to exert an axial biasing force onto the needle guard and the locking collar, the biasing member being configured to be engaged with the housing, wherein one end of the biasing member is engaged with a lip on the inner surface of the locking collar.

5. The needle assembly according to claim 4, wherein the at least one track comprises a first, a second, and a third path.

6. The needle assembly according to claim 4, comprising an outer sleeve which is configured to be fixed to the housing, the outer sleeve being configured to surround the locking collar and the biasing member, wherein the outer sleeve comprises at least one opening for viewing indicia provided on an outer surface of the locking collar, wherein the indicia are configured to indicate a pre-use ready position of the needle guard before an injection is performed and a locked position of the needle guard.

7. The needle assembly according to claim 6, wherein the at least one track comprises a first, a second, and a third path, wherein the needle guard is rotationally constrained by the outer sleeve and the locking collar is rotationally constrained when the at least one protrusion mechanically cooperates with the first path of the track, and wherein the assembly provides an audible or tactile indication when the locking collar rotates as the at least one protrusion moves from the first path to the second path.

8. The needle assembly according to claim 6, wherein the housing comprises an upper body and a lower body, wherein the lower body is connected to the upper body.

9. The needle assembly of claim 8, wherein the biasing member is adapted and arranged to be engaged with one of the upper body and the lower body and the outer sleeve is configured to be fixed to the lower body.

10. The needle assembly of claim 8, wherein the at least one track is provided by at least one of the upper body and the lower body.

11. The needle assembly according to claim 8, wherein the assembly comprises an inner cavity provided by the upper body and the lower body.

12. The needle assembly of claim 5, wherein the needle guard is axially moveable with respect to the housing between an extended and a retracted position, and wherein the at least one protrusion is configured to mechanically cooperate with the first and second path during retraction and partial extension of the needle guard.

13. The needle assembly of claim 5, wherein the at least one protrusion is configured to mechanically cooperate with the third path during final extension of the needle guard into a locking position where the needle guard is configured to be prevented from further axial movement with respect to the housing.

14. The needle assembly according to claim 5, wherein the locking collar is configured to rotate under at least one of the following conditions: the at least one protrusion moves from the first path to the second path; a biasing torque is created by mechanical interaction between the needle guard and the locking collar due to the biasing force exerted on the locking collar and the needle guard by the biasing member; a biasing torque is created by the biasing member or an additional biasing member.

15. The needle assembly according to claim 5, wherein the bearing surface comprises a crown arranged on the inner surface of the locking collar, and wherein the at least one surface comprises a plurality of angles surfaces, the crown being configured to mechanically cooperate with the plurality of angled surfaces to rotationally bias the locking collar.

16. The needle assembly according to claim 15, wherein, when the protrusion mechanically cooperates with the third path, the crown and the plurality of angled surfaces on the needle guard are configured to mechanically cooperate with each other, the collar and the needle guard being in a biasing relationship provided by the biasing member such that the needle guard is prevented from further axial movement, the needle assembly thus being in a post-use lock out state.

* * * * *